(12) United States Patent
Williams et al.

(10) Patent No.: US 6,657,075 B2
(45) Date of Patent: Dec. 2, 2003

(54) CONTINUOUS PROCESS FOR TERTIARY BUTYL ESTERS

(75) Inventors: Kevin Alan Williams, Mount Carmel, TN (US); Steven Leroy Cook, Kingsport, TN (US); Phillip Wayne Turner, Blountville, TN (US)

(73) Assignee: Eastman Chemical Company, Kingsport, TN (US)

(*) Notice: Subject to any disclaimer, the term of this patent is extended or adjusted under 35 U.S.C. 154(b) by 0 days.

(21) Appl. No.: 10/108,148

(22) Filed: Mar. 27, 2002

(65) Prior Publication Data

US 2002/0183544 A1 Dec. 5, 2002

Related U.S. Application Data

(63) Continuation-in-part of application No. 09/811,715, filed on Mar. 19, 2001.
(60) Provisional application No. 60/229,284, filed on Aug. 31, 2000.

(51) Int. Cl.$^7$ .......................... C07C 69/02; C07C 67/02; C07C 49/88
(52) U.S. Cl. .................... 560/231; 560/265; 568/302
(58) Field of Search ....................... 560/100, 103, 560/231, 265; 568/302

(56) References Cited

U.S. PATENT DOCUMENTS

| | | | |
|---|---|---|---|
| 2,018,759 A | 10/1935 | Frolich et al. | |
| 2,685,598 A | 8/1954 | Caldwell | |
| 3,031,495 A | 4/1962 | Young et al. | |
| 3,053,887 A | 9/1962 | Arles | |
| 3,055,934 A | 9/1962 | Heisler et al. | |
| 3,072,714 A | 1/1963 | Ruidisch et al. | |
| 3,096,365 A | 7/1963 | Heisler et al. | |
| 3,102,905 A | 9/1963 | Wheeler et al. | |
| 3,489,796 A | 1/1970 | Mazdiyasni et al. | |
| 3,590,073 A | 6/1971 | Carr et al. | |
| 3,679,739 A | 7/1972 | Schulz et al. | |
| 4,009,203 A | 2/1977 | Schmerling | |
| 4,360,406 A | 11/1982 | Ikeda et al. | |
| 5,151,547 A | 9/1992 | Sato et al. | |
| 5,840,962 A | 11/1998 | Cohen et al. | |
| 5,866,714 A | 2/1999 | Szady et al. | |

FOREIGN PATENT DOCUMENTS

| | | |
|---|---|---|
| DE | 3636754 | 5/1988 |
| GB | 1000913 | 8/1965 |

OTHER PUBLICATIONS

Webster's II New Riverside University Dictionary. Houghton Mifflin Company. pp. 480 and 627. (1994).*
The Merck Index, 13$^{th}$ ed. pp. 1539–1540. Merck & Co., Inc. Whitehouse Station, NJ (2001),*
Charles D. Hurd et al, "Ketene and Its Dimer", Northwestern University, Dec., 1939, pp. 3355–3359.
Satchell et al. J. Chem. Soc., B (1968), 889–897,.
F. O. Rice et al, "Ketene. I. Preparation and Reactions", J. Amer. Chem. Soc., vol. 56 (1934), pp. 1760–1765,.
L. Yu. Kryukova et al, "[2–Hydroxy–1,1,2,2–tetrakis(trifluoromethyl) ethoxy]carbonyl(trifluoromethyl) ketene", Zh. Vses. Khim. O–va, vol. 24 (1979), pp. 297–298 (Chemical Abstracts 91:123374).

* cited by examiner

Primary Examiner—Richard L. Raymond
Assistant Examiner—Zachary C. Tucker
(74) Attorney, Agent, or Firm—Eric D. Middlemas; Bernard J. Graves, Jr.

(57) ABSTRACT

Disclosed is a continuous process for the production of tertiary butyl esters by the reaction of a ketene and tertiary butyl alcohol containing a finite concentration of water. The process may be carried out in an absorber reactor with continuous recovery and purification of products by distillation. This process provides high-purity tertiary butyl acetate without the production of unwanted by-products found in many strong acid catalyzed processes.

5 Claims, 1 Drawing Sheet

CONTINUOUS PROCESS FOR TERTIARY BUTYL ESTERS

CROSS-REFERENCE TO RELATED APPLICATIONS

This application is a continuation-in-part of application Ser. No. 09/811,715, filed Mar. 19, 2001, incorporated herein by reference, which claims the benefit under 35 USC §119 of U.S. Provisional Application No. 60/229,284 filed Aug. 31, 2000.

FIELD OF THE INVENTION

This invention pertains to a process for the production of tertiary butyl esters. More specifically, this invention pertains to a continuous process for the preparation of tertiary butyl esters through the reaction of a ketene with tertiary butyl alcohol containing a finite amount of water.

BACKGROUND OF THE INVENTION

Carboxylic acid esters of tertiary butyl alcohol are useful for the production of agrochemicals, coatings, dyes, and solvents. There are several documented methods for the production of tertiary butyl esters. One well-known method for the preparation of tertiary butyl acetate (t-butyl acetate) is by the reaction of isobutylene with acetic acid in the presence of a variety of catalysts. Some of the many types of catalysts used for this reaction include metal silicates, cation exchange resins, acidic ion-exchange resins, sulfuric or other protic acids, as well as modified copolymers of styrene and divinylbenzene.

U.S. Pat. No. 5,866,714 describes a method for producing tertiary butyl acetate by the reaction of isobutylene with acetic acid using byproduct tertiary butyl alcohol to suppress olefin polymerization.

U.S. Pat. No. 4,360,406 describes a method for producing tertiary butyl alcohol and tertiary butyl acetate by the reaction of isobutylene with an aqueous solution of an aliphatic carboxylic acid in the presence of an acidic ion-exchange resin. In this process the t-butyl acetate is produced as a minor impurity, which is removed from the process by azeotropic distillation with water.

U.S. Pat. No. 4,009,203 describes a process for producing esters, including t-butyl acetate, by the reaction of an olefin with a halogenated aliphatic, halogenated aromatic or alkenic carboxylic acid in the presence of pre-formed acyloxystannic trihalide.

U.S. Pat. No. 3,102,905 describes a process for producing t-butyl acetate by the reaction of isobutylene and acetic acid in the presence of an organic sulfonic acid in the liquid phase. The crude product is then purified by means of distillation to give t-butyl acetate free of isobutylene.

U.S. Pat. No. 3,096,365 describes a process for producing tertiary esters from olefins and carboxylic acids in the presence of a polyvalent metal silicate catalyst. In this process a tertiary olefin is contacted with a carboxylic acid, in the presence of the catalyst, at temperatures not exceeding 300° F. to yield the corresponding tertiary ester.

U.S. Pat. No. 3,072,714 describes a process for separating esters from a mixture comprising the said ester, sulfuric acid, and an alkanoic acid. The ester is produced from the sulfuric acid catalyzed reaction of the alkanoic acid with an olefin. The ester is recovered by phase separation after treating the crude reaction mixture with an aqueous alkaline solution.

U.S. Pat. No. 3,055,934 describes a method for producing tertiary esters from tertiary olefins in the presence of sulfuric acid. In this process a tertiary olefin is condensed with an aliphatic hydrocarbylmonocarboxylic acid in the presence of sulfuric acid to produce the corresponding tertiary alkyl ester. The crude tertiary ester is recovered by phase separation after extraction with water.

U.S. Pat. No. 3,053,887 describes a method of producing a t-butyl ester from the reaction of an alkanoic acid with isobutylene in the presence of a catalyst. In this process isobutylene is reacted with a lower alkanoic acid in the presence of a sulfonated copolymer of styrene and a cross-linking compound consisting of divinylbenzene at a temperature below 5° C.

U.S. Pat. No. 3,031,495 describes a process for producing t-butyl acetate by the reaction of acetic acid with a tertiary olefin in the presence of a catalyst. In this process the acetic acid is contacted with the tertiary olefin at a temperature of 0–60° C. and in the presence of a catalyst consisting of a divinylbenzene cross-linked polystyrene sulfonic acid cationic exchange resin containing water.

In the related art described above, isobutylene (or other tertiary olefins) is reacted with acetic acid (or other carboxylic acids) in the presence of strongly acidic catalysts to yield t-butyl acetate (or other tertiary esters).

Another known method for producing esters is by the reaction of acetic acid with alcohols. The reaction of acetic acid with many primary and secondary alcohols proceeds readily, without catalyst, to yield the corresponding ester and water (byproduct). The reaction of tertiary alcohols with acetic acid, however, does not proceed at useful rates without the use of a strong acid catalyst. With t-butyl alcohol, the reaction of acetic acid proceeds smoothly with a variety of strong acid catalysts but yields are often low due to the formation of unwanted by-products, especially isobutylene. When tertiary butyl alcohol is reacted with acetic acid in the presence of strongly acidic catalysts, a large amount of isobutylene gas is formed from the acid-catalyzed dehydration of tertiary butyl alcohol. Due to the formation of the isobutylene, this process requires special equipment that allows for the recovery of the isobutylene off-gas in a safe manner and results in reduced yields.

The production of t-butyl acetate from acetic acid and tertiary butyl alcohol is described in several patents. U.S. Pat. No. 5,151,547 discloses a process for producing an organic carboxylic acid ester from an organic carboxylic acid and an alcohol in the presence of a catalytic amount of sulfuric acid in the gas phase. As described above, when tertiary butyl alcohol is reacted with acetic acid in the presence of a variety of acid catalysts, isobutylene gas was a major by-product. The separation of the by-product gas from the corresponding ester requires special equipment to allow for the recovery of the gas in a safe manner.

U.S. Pat. No. 3,590,073 discloses a method of producing t-butyl acetate from the reaction of acetic acid and tertiary butyl alcohol in the presence of a sulfonic acid cation exchange resin. When this method of production of t-butyl acetate is employed, temperatures exceeding >40° C. causes extensive decomposition of the product to isobutylene and acetic acid, which lowers yield dramatically.

German Patent Application No. 3,636,754 describes a continuous method of preparation of alkyl acetate from an alcohol and acetic acid in the presence of a mineral acid catalyst to yield the corresponding crude acetic acid ester. The crude ester is then purified by distillation.

In the related art described above, t-butyl acetate is produced by the reaction of a carboxylic acid with an alcohol in the presence of strong Lewis or mineral acid catalysts.

Another known method for the production of t-butyl acetate is by the reaction of acetic anhydride with tertiary butyl alcohol. This reaction proceeds without catalyst to yield t-butyl acetate and acetic acid. The major drawback of this method for producing t-butyl acetate is that for every mole of product produced, a mole of acetic acid by-product is also produced. A method for recovering the acetic acid must be developed to make the process economical. Another major drawback of this method for producing t-butyl acetate is that the reaction is somewhat sluggish, without the use of a catalyst, which restricts production rates. When a catalyst is used to improve the reaction rate, a variety of unwanted by-products are often produced making the production of pure t-butyl acetate more difficult without added purification equipment.

U.S. Pat. No. 3,489,796 describes a method for producing tertiary amyl acetate from acetic anhydride and tertiary amyl alcohol using hydrochloric acid as a catalyst. This method of producing tertiary amyl acetate gives product in good yield and high purity after fractional distillation.

In the related art discussed above, t-butyl acetate (or other tertiary esters) is produced by the reaction of acetic anhydride with tertiary butyl alcohol. The reaction between acetic anhydride and tertiary alcohols, including tertiary butyl alcohol, is somewhat sluggish and requires the use of an added catalyst to increase production rates. These catalysts often cause several unwanted by-products which makes the production of pure t-butyl acetate more difficult without added purification equipment.

Another known method for producing esters is by the direct reaction of an alcohol with a ketene. Ketene is an efficient acetylating agent toward many primary and secondary alcohols but it has been shown to be either non-reactive or very slow to react with tertiary alcohols, especially tertiary butyl alcohol, without the use of a catalyst. Strong acid catalysts, such as sulfuric acid or p-toluenesulfonic acid, are therefore commonly used to improve reaction rates (Hurd et al. J. Amer. Chem. Soc. 61 (1939) 3355–3359). Carboxylic acids also are known to catalyze the reaction between alcohols and dimethyl ketene (Satchell et al. J. Chem. Soc., B (1968), 889–897).

Rice et al. (J. Amer. Chem. Soc., 56 (1934), 1760), disclose the reaction of boiling tertiary butyl alcohol with ketene without added catalyst. Although under forcing conditions of temperature and concentration, the reaction was slow and incomplete and extensive polymerization of ketene was observed.

When an acid catalyst is used in the process for producing t-butyl acetate, the reaction proceeds more rapidly but often a large amount of isobutylene is observed as a byproduct from dehydration of the tertiary butyl alcohol. As stated before, a method for recovering the off-gas (isobutylene) would need to be implemented if t-butyl acetate is produced by this method on a large scale.

U.S. Pat. No. 2,018,759 describes a method of acetylation of liquid polyhydroxy aliphatic alcohols by means of a ketene. In this process a mixture of primary, secondary, and tertiary alcohols are treated with sufficient ketene to react with the primary alcohols. This mixture is then distilled, taking overhead the secondary and tertiary alcohols, and leaving the primary alcohol ester is the still bottom. The overhead mixture is then treated with ketene for a longer period of time, allowing for the reaction of the secondary alcohol with ketene to take place. In a similar operation as described above, the tertiary alcohol is distilled overhead leaving the secondary alcohol ester in the still bottom. This process is repeated until the tertiary alcohol is eventually converted to the tertiary acetate. This process requires mixtures of primary, secondary, and tertiary alcohols to be used in the process to produce primary, secondary, and eventually tertiary acetates after a long reaction time with the ketene. This process also requires several distillation and reaction steps.

U.S. Pat. No. 2,685,598 describes a method for preparing tertiary alcohol acetates by acetylating tertiary alcohols with ketene in the presence of a silica-alumina type catalyst. In this process ketene gas is contacted with a tertiary alcohol in the presence of the silica-alumina type catalyst. The products obtained from this reaction, which are mainly unreacted alcohol and the tertiary ester, are separated by means of distillation. The insoluble silica-alumina catalyst is then recovered by filtration.

U.S. Pat. No. 3,679,739 describes a method for producing esters of acetic acid by reacting ketene with alcohols in the presence of metal sulfides. In this process ketene gas is contacted with an alcohol and a mixture of the catalyst in a reactor apparatus. The mixture is stirred for a period of time, which can range from 30 minutes to 10 hours, and then the unreacted ketene is expelled from the mixture via a nitrogen purge. The ester product is then separated from the reaction mixture by means of distillation.

U.S. Pat. No. 5,840,962 describes a process for preparing an ester by the reaction of an alcohol with a ketene in an ester solvent in the presence of strong acid catalyst. In this process a mixture of alcohol and acid catalyst are continuously introduced into a reaction vessel in which ketene is also continuously introduced. The crude product is circulated to a refrigerator, or a second vessel, where excess ketene and a portion of the product (ester) are removed. Another portion of the product is re-circulated back to the reactor vessel for use as a solvent in the reaction. The acid catalyst used in this process is selected from a group consisting of sulfuric acid, toluenesulfonic acid, acetosulfuric acid, and other strong acids, and mixtures thereof. In the above-described processes, ketene and tertiary butyl alcohol are used as raw materials to produce t-butyl acetate, but all require strongly acidic catalysts to promote the reaction between the two.

The processes described above frequently rely on the use of strongly acidic homogeneous or hetergeneous catalysts to obtain reaction rates useful for commercial production of tertiary butyl esters. These catalysts often result in the production of by-products, such as isobutylene, which reduce yields and require additional expensive equipment to recover and purify the desired tertiary butyl ester. Thus, there is a need for an efficient and economical process for the production of tertiary butyl esters by the reaction of ketenes with tertiary butyl alcohol which is simple to operate and avoids the production of troublesome by-products.

BRIEF SUMMARY OF THE INVENTION

We have discovered a novel, continuous process for producing tertiary butyl esters by the reaction of ketenes with tertiary butyl alcohol comprising:

I. continuously feeding a gaseous ketene and a liquid reaction composition comprising t-butyl alcohol containing a finite concentration of water to a reaction zone to provide a product comprising an ester of tertiary butyl alcohol; and II. continuously removing said product from said reaction zone.

The present invention utilizes tertiary butyl alcohol containing a finite concentration of water as a starting material in an efficient, continuous process that provides tertiary butyl esters in high yield and assay. Without being bound by theory, the water present in the tertiary butyl alcohol reacts with the ketene to produce low concentrations of the corresponding carboxylic acid which may act as a catalyst for the esterification reaction but not as a catalyst for the production of by-products as observed with stronger mineral acids. In addition, the reaction of the ketene with carboxylic acids to form the corresponding anhydride maintains the concentration of carboxylic acid in the reaction mixture at a low but effective level which we believe further reduces the production of by-products. The present invention is especially useful for the preparation of tertiary butyl acetate by the reaction of ketene with tertiary butyl alcohol in a continuous process comprising:

I. continuously feeding gaseous ketene and a liquid reaction composition comprising t-butyl alcohol containing about 1 to 5 wt % water into an absorber reactor at a temperature of about 25 to 75° C. to give a product comprising tertiary butyl acetate; and
  II. continuously removing said product from said reaction zone.

Another preferred embodiment of the instant invention is a process for continuously recovering and refining the crude product of the absorber reactor by distillation to provide high purity tertiary butyl acetate and to separate unreacted tertiary butyl alcohol for recycle to the absorber reactor.

DETAILED DESCRIPTION OF THE INVENTION

Figure 1:
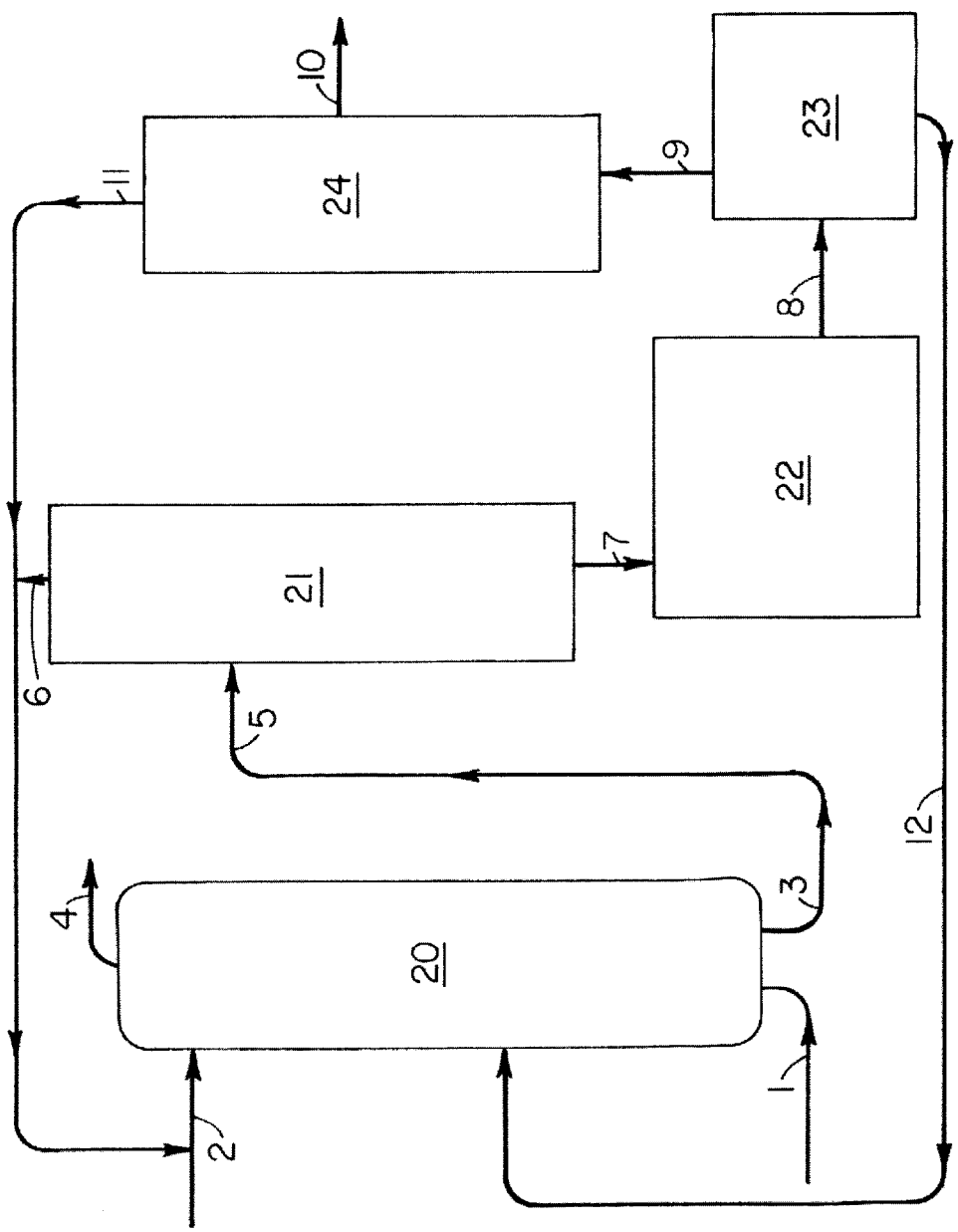
FIG. 1 shows a simple flow diagram and serves as an example illustrating the process steps for the continuous preparation and purification of tertiary butyl acetate as recited in the claims.

The present invention provides a continuous process for the preparation of tertiary butyl esters by the reaction of a ketene, in the vapor phase, with a liquid reaction composition comprising tertiary butyl alcohol containing a finite amount of water. In a general embodiment of the invention, our novel process comprises: continuously feeding a gaseous ketene and a liquid reaction composition comprising t-butyl alcohol containing a finite concentration of water to a reaction zone; continuously contacting said ketene with the liquid reaction composition to give a product comprising an ester of tertiary butyl alcohol; and continuously removing the product from the reaction zone. We have discovered that the presence of finite concentrations of water in the tertiary butyl alcohol, through the reaction with ketene, produces small amounts of carboxylic acids in situ which may serve as a mild catalyst for the esterification reaction of the ketene with tertiary butyl alcohol without catalyzing the formation of by-products. In addition, the reaction of ketene with any carboxylic acid present in the reaction milieu to produce the corresponding anhydride serves to maintain the concentration of acid at a constant but low level and further contributes to the high selectivities observed in the instant process. The use of an absorber reactor to achieve efficient gas-liquid contact in combination with the presence of water in the tertiary butyl alcohol results in an efficient process for the preparation of tertiary butyl esters in high conversions and selectivities.

Many ketenes are suitable for the process of the present invention. In general, any ketene of the formula

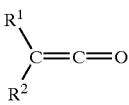

wherein R1 and R2 may be independently selected from alkyl groups consisting of 1 to 6 carbon atoms, aryl groups consisting of 6 to 10 carbon atoms, and mixtures thereof may be used in the present invention. Examples of useful ketenes include, but are not limited to, dimethylketene, diethylketene, methylethylketene, and diphenylketene. If the ketene is not in the gaseous state under standard conditions of temperature and pressure, the ketene is vaporized prior to introduction into the reactor. The preferred ketene is where R1 and R2 are hydrogen.

A variety of tertiary alcohols may be used as feedstocks for our novel process. Exemplary tertiary alcohols include tertiary amyl alcohol, 2-methyl-2-hydroxy pentane, 3-ethyl-3-hydroxy hexane; or unsaturated tertiary alcohols such as dimethyl vinyl carbinol, ethyl methyl vinyl carbinol; or tertiary alcohols containing an acetylenic linkage such as dimethyl ethinyl carbinol, ethyl methyl ethinyl carbinol, and mixtures thereof. The preferred tertiary alcohol is tertiary butyl alcohol containing a finite concentration of water which may be easily obtained from commercial sources. The term finite concentration of water is defined as a concentration of water substantially less than the concentration of tertiary butyl alcohol and which may vary from its initial value through the reaction of ketene and other components of the reaction mixture and thus only exist temporarily over the course of the reaction. The preferred water concentration within the tertiary butyl alcohol is from about 0.1 to 10 weight % with the most preferred range being from about 1.0 weight % to about 5 weight %. Commercially available tertiary butyl alcohol typically contains acetone, methanol, isopropanol, isobutyl alcohol and water. For example, a typical analysis of commercial tertiary butyl alcohol shows 95.0 wt % tertiary butyl alcohol, 1.5–2.0 wt % acetone, 0.3 wt % methanol, <0.1 wt % isopropanol, <0.1 wt % isobutyl alcohol, and 1.0–5.0 wt % water. More purified, anhydrous grades of tertiary butyl alcohol may also be used by adding water to within the preferred concentration range.

The temperature inside the reaction zone can range from 0–100° C., depending on the amount of heating or cooling placed on the exterior of the reactor. A particularly useful temperature range inside the reactor is from about 20° C. to about 80° C.; with the preferred temperature range of about 25° C. to about 75° C.

The reactor may be of any type which allows efficient continuous contact between liquid phase and gas phase reactants. The preferred reactor is an absorber reactor in which the ketene gas and liquid phases flow in countercurrent directions. An absorber reactor may be a plate column or a packed column containing stainless steel packing or other common column packing materials. Examples of suitable packing materials include, but are not limited to, structured metallic rings, metallic or ceramic saddles, glass or quartz beads, helices, tubes, and/or chips and the like.

In a preferred embodiment of the present invention, the product from the absorber reactor may be further recovered and purified by distillation through one or more distillation columns. A particularly preferred embodiment is described in detail and illustrated herein by reference to the drawing shown in FIG. 1 with particular reference to the continuous preparation of tertiary butyl acetate by the reaction of ketene with tertiary butyl alcohol with continuous recovery and purification by distillation.

Ketene gas is continuously fed through conduit (1) into the bottom of absorber reactor (20), while a liquid reaction composition comprising tertiary butyl alcohol is continuously fed via conduit (2) into the top of the reactor (20). The ketene and the liquid reaction composition flow in counter-current directions to achieve efficient gas-liquid contact, for example, as illustrated in FIG. 1 by ketene gas flowing upward through reactor (20) while the liquid composition flows downward. Unreacted ketene is removed from the top of the reactor through conduit (4) and may be recovered by means of an acetic acid scrubber (not shown), which converts ketene gas to acetic anhydride. The crude reaction product, comprising tertiary butyl acetate is removed continuously from the bottom of the reactor through conduit (3), and fed into a first distillation column (21) through conduit (5). Unreacted tertiary butyl alcohol containing low-boiling impurities is recovered at the top of distillation column (21) through conduit (6) and returned to reactor (20) via conduit (2). Crude tertiary butyl acetate is collected in still bottom (22) through conduit (7) and fed into still bottom (23) through conduit (8). A portion of the contents of still bottom (23) optionally may be recycled to reactor (20) through conduit (12). The crude tertiary butyl acetate is boiled from still bottom (23) through conduit (9) into a second distillation column (24). Purified tertiary butyl acetate is withdrawn from the middle of the distillation column through conduit (10). A less pure tertiary butyl acetate, containing a minor amount of impurities, is removed from the top of the column through conduit (11) where it may be recycled to reactor (20) via conduit (2).

Various low boiling impurities such as methyl acetate, isopropyl acetate, and isobutyl acetate may be formed from the reaction of ketene with various alcohol impurities typically present in commercial tertiary butyl alcohol. Any methyl acetate formed (from the reaction of trace quantities of methyl alcohol found in the crude tertiary butyl alcohol) is taken off at the top of the first distillation column (21) and recycled in the process. If the level of methyl acetate builds in the low boiler cut after a period of time, it can be taken off as a side-draw stream and sent for purification.

Any isopropyl and isobutyl acetate formed (from the reaction of trace quantities of isopropyl and isobutyl alcohol found in the tertiary butyl alcohol) are taken off at the top of the first distillation column and at the top of the second distillation column and recycled in the process. If the level of each ester builds in either of the columns, they may be taken off as side-draw streams from the columns and further purified.

The normal by-products from the reaction of tertiary butyl alcohol and ketene, using the method of the present invention, are typically methyl acetate ($\leq 0.1$ wt %), isopropyl acetate ($\leq 0.3$ wt %), isobutyl acetate ($\leq 0.2$ wt %), acetic acid ($\leq 0.3$ wt %), and acetic anhydride ($\leq 2.0$ wt %).

Any acetic acid formed (from the reaction of water in the tertiary butyl alcohol) and any acetic anhydride formed (from the reaction of acetic acid with ketene) are by-products that are collected in the still bottom (23) of the second distillation column. The minor amounts of acetic acid and acetic anhydride thus formed in situ may be recycled back to the beginning of the process for further reaction to yield t-butyl acetate or may be purged from the system and recovered. The preferred process is to purge and recover the acetic acid and acetic anhydride from the second distillation column still bottom.

This invention can be further illustrated by the following examples of preferred embodiments thereof, although it will be understood that these examples are included merely for purposes of illustration and are not intended to limit the scope of the invention unless otherwise specifically indicated.

EXAMPLES

Example 1

This example demonstrates the ability to prepare t-butyl acetate from ketene and tertiary butyl alcohol (95.0 wt % tertiary butyl alcohol, 1.5–2.0 wt % acetone, 0.3 wt % methanol, <0.1 wt % isopropanol, <0.1 wt % isobutyl alcohol, and 1.0–5.0 wt % water) in a continuous mode, without the addition of a catalyst to promote the reaction. The absorber reactor(20) in this experiment was a glass tube packed with 316 stainless Penn State packing. The height of the reactor was 50 cm (20 in.) and the diameter was 2.5 cm. The ketene was fed (1) into the bottom of the reactor at a rate of 45.8 grams/hour and the tertiarybutyl alcohol was fed (2) into the top of the reactor at a rate of 88.0 ml/hour. The crude product was continuously collected (3) at the bottom of the reactor via a fritted glass inlet. The crude product was collected at a rate of 87.0 ml/hour. The temperature in the reaction zone was 30° C. to 35° C. throughout the reaction. The reaction data is shown below in Table 1.

TABLE 1

Reaction of ketene and tertiary butyl alcohol

| Time (min.) | Alcohol (ml) | Ketene (g) | Crude Product (ml) |
|---|---|---|---|
| 0 | 0 | 0.0 | 0 |
| 30 | 39 | 19.2 | 15 |
| 60 | 87 | 42.9 | 67 |
| 90 | 130 | 70.1 | 115 |
| 120 | 171 | 92.9 | 164 |
| 150 | 221 | 122.7 | 213 |
| 163 | 239 | 124.5 | 236* |

*crude product analyzed at this point

The reaction mixture was analyzed by gas chromatography (Column DB-1701, 30m×0.25 mm×1 $\mu$m, Inj. Temp.= 250° C., Inj. Amt.=0.5 $\mu$L neat). Analysis of the crude reaction mixture showed 30.5 wt % t-butyl acetate, 65.1 wt % tertiary butyl alcohol, 0.2 wt % acetic acid, 1.6 wt % acetic anhydride, and approximately 2.6 wt % unknowns. The yield of this reaction was determined to be 88.0 wt % based on the amount of tertiary butyl alcohol reacted.

Example 2

The absorber reactor (20) in this experiment was the same reactor as described in Example 1. The ketene was fed (1) into the bottom of the reactor at a rate of 34.4 grams/hour and the tertiarybutyl alcohol was fed (2) into the top of the reactor at a rate of 74.0 ml/hour. The crude product was continuously collected (3) at the bottom of the reactor via a fritted glass inlet. The crude product was collected at a rate of 74.0 ml/hour (Step 3). The temperature in the reaction zone was 30° C. to 35° C. throughout the reaction. The data is shown below in Table 2.

TABLE 2

Reaction of ketene and tertiary butyl alcohol

| Time (min.) | Alcohol (ml) | Ketene (g) | Crude Product (ml) |
|---|---|---|---|
| 0 | 0 | 0.0 | 0 |
| 30 | 38 | 14.0 | 12 |
| 60 | 76 | 32.4 | 52 |
| 90 | 110 | 48.2 | 92 |
| 120 | 148 | 64.9 | 130 |
| 150 | 187 | 82.4 | 170 |
| 210 | 253 | 116.6 | 237 |

TABLE 2-continued

Reaction of ketene and tertiary butyl alcohol

| Time (min.) | Alcohol (ml) | Ketene (g) | Crude Product (ml) |
|---|---|---|---|
| 270 | 329 | 153.4 | 320 |
| 320 | 396 | 183.2 | 395* |

*crude product analyzed at this point

The reaction mixture was analyzed by gas chromatography. Analysis of the crude reaction mixture showed 30.7 wt % t-butyl acetate, 65.2 wt % tertiary butyl alcohol, 0.2 wt % acetic acid, 1.5 wt % acetic anhydride, 0.3 wt % acetone, 0.2 wt % isopropyl acetate, 0.2 wt % isobutyl acetate, and approximately 1.7 wt % unknowns. The yield of this reaction was determined to be 91.3 wt % based on the amount of tertiary butyl alcohol reacted.

Example 3

This example demonstrates the ability to prepare relatively high purity (>98 wt %) t-butyl acetate from ketene and tertiary butyl alcohol in a continuous mode, without the addition of a catalyst to promote the reaction. The absorber reactor (20) in this experiment was the same as that described in Example 1. In this example the crude product, which was prepared under the same reactor conditions described in Example 1, was continuously fed into a low-boiler removal column (21). The low-boilers were removed (6) at the top of the low-boiler removal column and the t-butyl acetate was removed via a short refining column (not shown) attached to the same low-boiler removal column still bottom (22). The tertiary butyl alcohol was fed into the top of the absorber reactor at a rate of 80-ml/hour and the ketene was fed into the bottom of the absorber reactor at a rate of 32.1 grams/hour.

The crude product (30.5 wt % t-butyl acetate) was collected (3) in a graduated cylinder at the bottom of the reactor and was continuously fed (5) into the low-boiler removal column at a rate of 80.0-ml/hour. The temperature at the feed point of crude product into the low-boiler removal column was 94° C. The low boilers from the crude product (85.9 wt % tertiary butyl alcohol, 0.2 wt % acetone, 0.3 wt % isopropyl acetate, 12.2 wt % t-butyl acetate, and 0.1 wt % acetic acid) were removed (6) at the top of the low-boiler removal column by controlling the head temperature of the column at 84–85° C. The low-boiler take-off rate was 54.0-ml/hour.

The t-butyl acetate, which accumulated in the low-boiler removal column (21) at a temperature of 108–110° C., was removed via a short refining column (not shown). The t-butyl acetate was removed at the top of the short refining column by controlling its head temperature at 96–98° C. The t-butyl acetate take-off rate was 24.0-ml/hour.

The analysis of the t-butyl acetate showed 98.4 wt % t-butyl acetate, 0.2 wt % tertiary butyl alcohol, 0.2 wt % acetone, 0.3 wt % acetic acid, 0.2 wt % isobutyl acetate, 0.2 wt % acetic anhydride, and 0.5 wt % unknowns Example 4

The absorber reactor (20) in this experiment was the same reactor as described in Example 1 except that a packed column (not shown) was added on top of the absorber reactor. A thermocouple was placed between the absorber reactor and the packed column. The total reactor height was 95 cm (38 in.). The ketene was fed (1) into the bottom of the reactor at a rate of 14.6 grams/hour and the tertiary butyl alcohol was fed (2) into the top of the reactor at a rate of 62.0 ml/hour. The crude product was continuously collected (3) at the bottom of the reactor via a fritted glass inlet. The crude product was collected at a rate of 62.0 ml/hour. The temperature in the reaction zone was 29–35° C. throughout the reaction. The reaction data is shown below in Table 3.

TABLE 3

Reaction of ketene and tertiary butyl alcohol

| Time (min.) | Alcohol (ml) | Ketene (g) | Crude Product (ml) |
|---|---|---|---|
| 0 | 0 | 0.0 | 0 |
| 30 | 30 | 6.1 | 0 |
| 60 | 60 | 14.0 | 45 |
| 120 | 125 | 29.8 | 106 |
| 188 | 192 | 46.5 | 179 |
| 242 | 250 | 59.7 | 235 |
| 270 | 279 | 65.8 | 279 |

*crude product sampled and analyzed at this point

The reaction mixture was analyzed by gas chromatography. Analysis of the crude reaction mixture showed 42.4 wt % t-butyl acetate, 53.9 wt % tertiary butyl alcohol, 0.2 wt % acetic acid, 1.0 wt % acetic anhydride, and 2.5 wt % unknowns.

Example 5

The absorber reactor (20) in this experiment was the same reactor as described in Example 4. In this experiment, the crude t-butyl acetate was recycled back through the absorber reactor at a rate of 11.3 ml/hour (optional step not shown). The ketene was fed (1) into the bottom of the reactor at a rate of 14.7 grams/hour and the tertiary butyl alcohol was fed (2) into the top of the reactor at a rate of 44.0 ml/hour. The crude product was continuously collected (3) at the bottom of the reactor via a fritted glass inlet. The crude product was collected at a rate of 51.3 ml/hour. The temperature in the reaction zone was 27–29° C. throughout the reaction. The reaction data is shown below in Table 4.

TABLE 4

Reaction of ketene and tertiary butyl alcohol

| Time (min.) | Alcohol (ml) | Ketene (g) | Crude Product Recycled (ml)# | Crude Product Collected (ml) |
|---|---|---|---|---|
| 0 | 0 | 0.0 | 0 | 0 |
| 30 | 22 | 7.9 | 6 | 24 |
| 60 | 45 | 13.2 | 12 | 50 |
| 90 | 65 | 21.1 | 17 | 75 |
| 124 | 90 | 29.9 | 23 | 102 |
| 150 | 111 | 35.2 | 28 | 119* |
| 180 | 132 | 44.0 | 34 | 154 | assay of crude product recycled = 39.9 wt % t-butyl acetate and 56.5 wt % tertiary butyl alcohol
*crude product sampled and analyzed by GC at this point The reaction mixture was analyzed by gas chromatography. Analysis of the crude reaction mixture showed 49.2 wt % t-butyl acetate, 44.5 wt % tertiary butyl alcohol, 0.14 wt % acetic acid, 2.4 wt % acetic anhydride, and 3.76 wt % unknowns.

This example clearly demonstrates that crude t-butyl acetate can be continuously produced by the uncatalyzed reaction of tertiary butyl alcohol with ketene in an absorber reactor. This example also demonstrates that the crude product can be recycled through the absorber reactor at a given rate, which can increase the percentage of t-butyl acetate found in the crude product.

Example 6

The absorber reactor (20) in this experiment was the same reactor as described in Example 4. In this experiment, the crude t-butyl acetate was recycled back through the absorber reactor at a rate of 20.8 ml/hour (optional step not shown). The ketene was fed (1) into the bottom of the reactor at a rate of 11.5 grams/hour and the tertiary butyl alcohol was fed (2) into the top of the reactor at a rate of 48.0 ml/hour. The crude product was continuously collected (3) at the bottom of the reactor via a fritted glass inlet. The crude product was collected at a rate of 66.4 ml/hour. The temperature in the reaction zone was 27–31° C. throughout the reaction. The reaction data is shown below in Table 5.

TABLE 5

Reaction of ketene and tertiary butyl alcohol

| Time (min.) | Alcohol (ml) | Ketene (g) | Crude Product Recycled (ml)# | Crude Product Collected (ml) |
|---|---|---|---|---|
| 0 | 0 | 0.0 | 0 | 0 |
| 30 | 25 | 1.8 | 6 | 11 |
| 60 | 50 | 9.6 | 13 | 50 |
| 90 | 75 | 14.8 | 20 | 84 |
| 120 | 100 | 21.8 | 30 | 119 |
| 180 | 145 | 33.1 | 55 | 193 |
| 240 | 190 | 44.4 | 81 | 263* |
| 300 | 240 | 57.5 | 104 | 332 | assay of crude product recycled = 39.2 wt % t-butyl acetate and 56.5 wt % tertiary butyl alcohol
*crude product sampled and analyzed by GC at this point The reaction mixture was analyzed by gas chromatography. Analysis of the crude reaction mixture showed 40.8 wt % t-butyl acetate, 54.1 wt % tertiary butyl alcohol, 0.25 wt % acetic acid, 1.92 wt % acetic anhydride, and 2.93 wt % unknowns.

This example demonstrates that crude t-butyl acetate can be continuously produced by the uncatalyzed reaction of tertiary butyl alcohol with ketene in an absorber reactor. This example also demonstrates that the rate at which the crude product is recycled back through the absorber reactor can increase the percentage of t-butyl acetate found in the crude product.

Example 7

The absorber reactor (20) in this experiment was the same reactor as described in Example 4. The crude product was not recycled back through the absorber reactor in this experiment. The ketene was fed (1) into the bottom of the reactor at a rate of 22.8 grams/hour and the tertiary butyl alcohol was fed (2) into the top of the reactor at a rate of 124.6 ml/hour. The crude product was continuously collected (3) at the bottom of the reactor via a fritted glass inlet. The crude product was collected at a rate of 105.6 ml/hour. The temperature in the absorber reactor was 39–45° C. throughout the reaction. The temperature between the absorber reactor and the added column was 67–72° C. throughout the reaction. The reaction data is shown below in Table 6.

TABLE 6

Reaction of ketene and tertiary butyl alcohol

| Time (min.) | Alcohol (ml) | Ketene (g) | Crude Product (ml) |
|---|---|---|---|
| 0 | 0 | 0.0 | 0 |
| 60 | 137 | 21.9 | 119 |
| 90 | 202 | 34.2 | 185 |

TABLE 6-continued

Reaction of ketene and tertiary butyl alcohol

| Time (min.) | Alcohol (ml) | Ketene (g) | Crude Product (ml) |
|---|---|---|---|
| 120 | 262 | 45.6 | 242 |
| 180 | 379 | 71.0 | 329 |
| 210 | 438 | 83.3 | 370* |
| 240 | 497 | 93.8 | 419 |
| 300 | 623 | 114.0 | 528 |

*crude product sampled and analyzed by GC at this point

The reaction mixture was analyzed by gas chromatography. Analysis of the crude reaction mixture showed 45.7 wt % t-butyl acetate, 49.2 wt % tertiary butyl alcohol, 0.25 wt % acetic acid, 1.87 wt % acetic anhydride, and 2.98 wt % unknowns. The yield of this reaction was determined to be 92.9 wt % based on the amount of tertiary butyl alcohol reacted.

Example 8

The absorber reactor (20) in this experiment was a 100-cm (40 in.) Penn State column packed with 316 stainless steel packing. The crude product was not recycled back through the absorber reactor in this example. The ketene was fed (1) into the bottom of the reactor at a rate of 24.0 grams/hour and the tertiary butyl alcohol was fed (2) into the top of the reactor at a rate of 117.4 ml/hour. The crude product was continuously collected (3) at the bottom of the reactor via a fritted glass inlet. The crude product was collected at a rate of 115.8 ml/hour. The temperature in the reaction zone was 49–74° C. (range from top to bottom) throughout the reaction. The reaction data is shown below in Table 7.

TABLE 7

Reaction of ketene and tertiary butyl alcohol

| Time (min.) | Alcohol (ml) | Ketene (g) | Crude Product (ml) |
|---|---|---|---|
| 0 | 0 | 0.0 | 0 |
| 30 | 63 | 10.5 | 40 |
| 60 | did not read | 22.8 | 100 |
| 90 | 178 | 35.1 | 160 |
| 120 | 238 | 45.6 | 216 |
| 210 | 408 | 83.3 | 388 |
| 240 | 468 | 95.6 | 451* |
| 300 | 587 | 120.2 | 579 |

*crude product sampled and analyzed by GC at this point

The reaction mixture was analyzed by gas chromatography. Analysis of the crude reaction mixture showed 35.7 wt % t-butyl acetate, 59.3 wt % tertiary butyl alcohol, 0.23 wt % acetic acid, 1.92 wt % acetic anhydride, and 2.85 wt % unknowns. The yield of this reaction was determined to be 92.1 wt % based on the amount of tertiary butyl alcohol reacted.

Example 9

The absorber reactor (20) in this experiment was the same as that used in Example 8. The crude product was not recycled back through the absorber reactor in this example. The ketene was fed (1) into the bottom of the reactor at a rate of 21.9 grams/hour and the tertiary butyl alcohol was fed (2) into the top of the reactor at a rate of 104.4 ml/hour. The crude product was continuously collected (3) at the bottom of the reactor via a fritted glass inlet. The crude product was collected at a rate of 102.6 ml/hour. The temperature in the reaction zone was 39–73° C. (range from top to bottom) throughout the reaction. The reaction data is shown below in Table 8.

TABLE 8

Reaction of ketene and tertiary butyl alcohol

| Time (min.) | Alcohol (ml) | Ketene (g) | Crude Product (ml) |
|---|---|---|---|
| 0 | 0 | 0 | 0 |
| 30 | 52 | 10.5 | 50 |
| 60 | 103 | 21.9 | 95 |
| 90 | 157 | 35.0 | 149 |
| 120 | 210 | 45.5 | 199 |
| 180 | 312 | 70.0 | 304 |
| 210 | 367 | 78.8 | 359 |
| 300 | 522 | 109.4 | did not read |

*crude product sampled and analyzed by GC at this point

The reaction mixture was analyzed by gas chromatography. Analysis of the crude reaction mixture showed 36.9 wt % t-butyl acetate, 58.1 wt % tertiary butyl alcohol, 0.22 wt % acetic acid, 2.04 wt % acetic anhydride, and 2.74 wt % unknowns. The yield of this reaction was determined to be in excess of 100 wt % based on the amount of tertiary butyl alcohol reacted.

Example 10

This example demonstrates the ability to continuously refine the crude t-butyl acetate produced in Examples 1, 2, 4, 5, 6, 7, 8, and 9. This example excludes steps 8, 9, and 10 shown in FIG. 1. The low boiler removal column still bottom (22) was filled with pure t-butyl acetate (99.4%) before the continuous refining process was started. The crude t-butyl acetate (60.6 wt % tertiary butyl alcohol, 34.9 wt % t-butyl acetate, 0.5 wt % acetic acid, and 1.6 wt % acetic anhydride) was fed (5) into the low boiler removal column at a rate of 75.5 ml/hour and at a temperature range of 84–93° C. The low boilers were removed (6) at a rate of 56.0 ml/hour and at a temperature range of 79° C. to 82° C.

The t-butyl acetate was removed from the low boiler column still bottom (22) via a short refining column (not shown) at a rate of 40.0 ml/hour and at a temperature range of 95–97° C. Analysis of the low boilers (6) after running continuously for 5.5 hours showed 86.4 wt % tertiary butyl alcohol, 11.8 wt % t-butyl acetate, 0.0 wt % acetic acid, and 0.0 wt % acetic anhydride. Analysis of the t-butyl acetate taken off the top of the short refining column after running continuously for 5.5 hours showed 99.3 wt % t-butyl acetate, 0.1 wt % tertiary butyl alcohol, 0.1 wt % acetic acid, and 0.08 wt % acetic anhydride. The continuous method was stopped after 5.5 hours and a sample from the low boiler removal column still bottom (22) was taken. Analysis of this sample showed 87.5 wt % t-butyl acetate, 2.7 wt % acetic acid, and 3.5 wt % acetic anhydride.

Example 11

This example demonstrates the ability to continuously refine the crude t-butyl acetate produced in Examples 1, 2, 4, 5, 6, 7, 8, and 9. This example also excludes steps 8, 9, and 10 shown in FIG. 1. The low boiler removal column still bottom (22) was filled with material containing 87.5 wt % t-butyl acetate, 2.7 wt % acetic acid, and 3.5 wt % acetic anhydride before the continuous refining process was started. The crude t-butyl acetate (60.6 wt % tertiary butyl alcohol, 34.9 wt % t-butyl acetate, 0.5 wt % acetic acid, and 1.6 wt % acetic anhydride) was fed (5) into the low boiler removal column at a rate of 95.2 ml/hour and at a temperature range of 91° C. to 95° C. The low boilers were removed (6) at a rate of 67.8 ml/hour and at a temperature range of 82° C. to 84° C.

The t-butyl acetate was removed from the low boiler column still bottom (22) via a short refining column (not shown) at a rate of 39.7 ml/hour and at a temperature range of 96° C. to 98° C. Analysis of the low boilers (6) after running continuously for 6.25 hours showed 80.4 wt % tertiary butyl alcohol, 17.8 wt % t-butyl acetate, 0.0 wt % acetic acid, and 0.0 wt % acetic anhydride. Analysis of the t-butyl acetate taken off of the top of the short refining column after running continuously for 6.25 hours showed 99.0 wt % t-butyl acetate, 0.1 wt % tertiary butyl alcohol, 0.1 wt % acetic acid, and 0.0 wt % acetic anhydride. The continuous process was stopped after 6.25 hours and a sample from the low boiler removal column still bottom (22) was taken. Analysis of this sample showed 83.8 wt % t-butyl acetate, 3.3 wt % tertiary butyl alcohol, 3.6 wt % acetic acid, and 5.4 wt % acetic anhydride.

Example 12

This example demonstrates the ability to continuously refine the crude t-butyl acetate produced as described in Examples 1, 2, 4, 5, 6, 7, 8, and 9. The low boiler removal column still bottom(22) was filled with pure t-butyl acetate (99.4 wt %) before the continuous refining process was started. The crude t-butyl acetate (22.62 wt %) was fed (5) into the low boiler removal column at a rate of 104.9 ml/hour and at a temperature range of 91° C. to 92° C. The low boilers were removed (6) at a rate of 92.9 ml/hour and at a temperature range of 82° C. to 83° C.

The t-butyl acetate was removed from the low boiler removal column still bottom (22) and fed (8) into the refining column still bottom (23) at a rate of 26.7 ml/hour and a temperature range of 98–99° C. The analysis of the material fed into the refining column still bottom (23) showed 98.8 wt % t-butyl acetate, 0.02 wt % tertiary butyl alcohol, 0.33 wt % acetic acid, and 0.48 wt % acetic anhydride. The material in the refining column still bottom (23) was removed (10) via a side-draw off of the refining column (24). The t-butyl acetate was removed at the side-draw of the refining column at a rate of 13.3 ml/hour and a temperature of 98° C. The t-butyl acetate containing a small amount of tertiary butyl alcohol was removed (11) at the top of the refining column (24) at a rate of 2.7 ml/hour and a temperature of 95° C. Analysis of the low boilers (6) after running continuously for 5.5 hours showed 85.0 wt % tertiary butyl alcohol, 12.8 wt % t-butyl acetate, 0.0 wt % acetic acid, and 0.0 wt % acetic anhydride.

Analysis of the t-butyl acetate side-draw (10) after running continuously for 4.5 hours showed 99.3 wt % t-butyl acetate, 0.0 wt % tertiary butyl alcohol, 0.0 wt % acetic acid, and 0.0 wt % acetic anhydride. Analysis of the t-butyl acetate taken (11) at the top of the refining column (24) after running continuously for 4.5 hours showed 91.6 wt % t-butyl acetate, 3.2 wt % tertiary butyl alcohol, 0.0 wt % acetic acid, and 0.0 wt % acetic anhydride.

Example 13

This example demonstrates the ability to continuously refine the crude t-butyl acetate produced in Examples 1, 2, 4, 5, 6, 7, 8, and 9. The low boiler removal column still bottom (22) contained the same material as that of Example 12 before the continuous refining process was started. The crude t-butyl acetate (72.9 wt % tertiary butyl alcohol, 22.6 wt % t-butyl acetate, 0.7 wt % acetic acid, and 1.1 wt % acetic anhydride) was fed (5) into the low boiler removal column at a rate of 109.2 ml/hour and at a temperature range of 90° C. to 95° C. The low boilers were removed (6) at a rate of 92.5 ml/hour and at a temperature range of 82° C. to 83° C.

The t-butyl acetate was removed from the low boiler removal column still bottom (22) and fed (8) into the refining column still bottom (23) at a rate of 27.8 ml/hour and a temperature range of 99° C. to 101° C. Analysis of the material fed (8) into the refining column still bottom (23) showed 95.5 wt % t-butyl acetate, 0.3 wt % tertiary butyl alcohol, 1.3 wt % acetic acid, and 1.7 wt % acetic anhydride. The material in the refining column still bottom (23) was removed (1) via a side-draw off of the refining column (24). The t-butyl acetate was removed at the side-draw of the refining column at a rate of 26.0 ml/hour and a temperature of 98° C. The t-butyl acetate containing a small amount of tertiary butyl alcohol was removed (11) at the top of the refining column at a rate of 1.8 ml/hour and a temperature of 95° C. Analysis of the low boilers (6) after running continuously for 6.0 hours showed 84.5 wt % tertiary butyl alcohol, 13.5 wt % t-butyl acetate, 0.0 wt % acetic acid, and 0.0 wt % acetic anhydride.

Analysis of the t-butyl acetate taken at the side-draw (10) of the refining column (24) after running continuously for 5.0 hours showed 99.6 wt % t-butyl acetate, 0.02 wt % tertiary butyl alcohol, 0.0 wt % acetic acid, and 0.0 wt % acetic anhydride. Analysis of the t-butyl acetate taken (11) at the top of the refining column (24) after running continuously for 5.0 hours showed 95.1 wt % t-butyl acetate, 3.2 wt % tertiary butyl alcohol, 0.0 wt % acetic acid, and 0.0 wt % acetic anhydride.

Example 14

This example demonstrates the ability to continuously refine the crude t-butyl acetate produced in Examples 1, 2, 4, 5, 6, 7, 8, and 9. The low boiler removal column still bottom (22) contained the same material as that of Example 13 before the continuous refining process was started. The crude t-butyl acetate (72.9 wt % tertiary butyl alcohol, 22.6 wt % t-butyl acetate, 0.7 wt % acetic acid, and 1.1 wt % acetic anhydride) was fed (5) into the low boiler removal column (22) at a rate of 109.5 ml/hour and at a temperature range of 88° C. to 95° C. The low boilers were removed (6) at a rate of 92.6 ml/hour and at a temperature range of 81° C. to 83° C.

The t-butyl acetate was removed from the low boiler removal column still bottom (22) and fed (8) into the refining column still bottom (23) at a rate of 27.6 ml/hour and a temperature range of 99–101° C. The analysis of the material fed into the refining column still bottom showed 93.6 wt % t-butyl acetate, 0.2 wt % tertiary butyl alcohol, 1.8 wt % acetic acid, and 2.4 wt % acetic anhydride. The material in the refining column still bottom was removed (10) via a side-draw off of the refining column (24). The t-butyl acetate was removed at the side-draw of the refining column at a rate of 25.7 ml/hour and a temperature of 98° C. The t-butyl acetate containing a small amount of tertiary butyl alcohol was removed (11) at the top of the refining column (24) at a rate of 1.9 ml/hour and a temperature of 95° C. Analysis of the low boilers (6) after running continuously for 4.75 hours showed 85.1 wt % tertiary butyl alcohol, 12.8 wt % t-butyl acetate, 0.0 wt % acetic acid, and 0.0 wt % acetic anhydride.

Analysis of the t-butyl acetate taken (10) at the side-draw of the refining column (24) after running continuously for 4.75 hours showed 99.5 wt % t-butyl acetate, 0.03 wt % tertiary butyl alcohol, 0.0 wt % acetic acid, and 0.0 wt % acetic anhydride. Analysis of the t-butyl acetate taken off (11) at the top of the refining column (24) after running continuously for 4.75 hours showed 95.6 wt % t-butyl acetate, 3.5 wt % tertiary butyl alcohol, 0.0 wt % acetic acid, and 0.0 wt % acetic anhydride.

In the drawings and specification, there have been disclosed typical preferred embodiments of the invention and, although specific terms are employed, they are used in a generic and descriptive sense only and not for purposes of limitation, the scope of the invention being set forth in the following claims.

We claim:

1. Continuous process for preparing tertiary butyl acetate comprising:

I. continuously feeding gaseous ketene and a liquid reaction composition comprising t-butyl alcohol containing about 1 to 10 wt % water into an absorber reactor at a temperature of about 0 to 100° C. to provide a product comprising tertiary butyl acetate; and II. continuously removing said product from said reaction zone.

2. Process according to claim 1 wherein said absorber reactor is a packed column or a plate column.

3. Process according to claim 2 wherein said gaseous ketene is contacted with said liquid reaction medium in a countercurrent flow.

4. Process according to claim 3 further comprising

I. continuously feeding said product from said reaction zone of Step II to a first distillation column;

II. continuously removing a lower boiling component comprising tertiary butyl alcohol from the top of said first distillation column III. continuously removing a higher boiling component from the bottom of said first distillation column comprising tertiary butyl acetate IV. recycling said lower boiling component to said absorber reactor.

5. Process according to claim 4 further comprising

I. continuously feeding said higher boiling component from said first distillation column to a second distillation column;

II. continuously removing from the top of said second distillation column a lower boiling component comprising tertiary butyl acetate containing lower boiling impurities; and III, continuously removing from the middle of said second distillation column a higher boiling component comprising tertiary butyl acetate;

IV. recycling said lower boiling component from said second distillation column to said absorber reactor.

* * * * *